(12) United States Patent
Quinn et al.

(10) Patent No.: US 6,331,647 B1
(45) Date of Patent: Dec. 18, 2001

(54) PROCESS FOR THE PREPARATION OF A PURIFIED ACRYLAMIDO SULFONIC ACID MONOMER DERIVATIVE

(75) Inventors: Robert E. Quinn, Cleveland; W. Michael Burke, Chardon, both of OH (US); William S. Henry, Houston, TX (US); Steven A. Goodlive, Lakewood, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 08/355,712

(22) Filed: Dec. 14, 1994

Related U.S. Application Data

(63) Continuation-in-part of application No. 07/709,745, filed on Jun. 3, 1991, now abandoned.
(51) Int. Cl.[7] .................................................. C07C 309/15
(52) U.S. Cl. ............................................................ 562/105
(58) Field of Search ............................................... 562/105

(56) References Cited

U.S. PATENT DOCUMENTS 4,701,283 * 10/1987 Itoh et al. ............................ 562/105

* cited by examiner

Primary Examiner—Robert Gerstl
(74) Attorney, Agent, or Firm—David M. Shold

(57) ABSTRACT

A process for the preparation of a purified monomer is disclosed which comprises the steps of reacting an impure monomer (A)

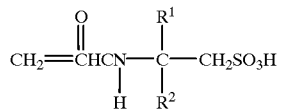

wherein $R^1$ and $R^2$ are independently hydrogen or alkyl groups containing from 1 to about 6 carbon atoms, with (B) a substantially aqueous solution of an oxide or hydroxide of the structure MO or MOH wherein M is a Group IA or Group IIA metal, or an amine of the structure $NR^3R^4R^5$ wherein $R^3$, $R^4$ and $R^5$ are independently hydrogen or alkyl, alkanol or alkoxy groups containing from 1 to about 12 carbon atoms, wherein the molar ratio of (A):(B) is from about 1:1–2 for Group IA metals, 2:1–2 for Group IIA metals or ratio of moles of (A) to nitrogens of (B) is from about 1:1–2 nitrogens to form a salt, wherein in order to prevent polymerization of (A), the purified monomer or both or prevent undesired side reactions, the reaction of (A) and (B) occurs at a temperature of between about −20 to 75° C. and at a pH between about 7 to about 12.5, and recovering a purified salt by crystallization in the presence of an oxygen bearing gas stream by subjecting the aqueous solution to changes in temperature and/or pressure and/or concentration.

18 Claims, 2 Drawing Sheets

PROCESS FOR THE PREPARATION OF A PURIFIED ACRYLAMIDO SULFONIC ACID MONOMER DERIVATIVE

This is a continuation-in-part of application Ser. No. 07/709,745 filed on Jun. 3, 1991, now abandoned.

FIELD OF THE INVENTION

This invention relates to a process for preparing a purified sulfonic acid monomer salt. The purification is accomplished by a crystallization of a derivative of the monomer from an aqueous solution.

BACKGROUND OF THE INVENTION

Previously purified derivatives of acrylamido sulfonic acid monomers are prepared utilizing the already purified sulfonic acid.

U.S. Pat. No. 4,337,215 (Doi et al, Jun. 29, 1982) relates to a purification process for the efficient preparation of high-purity 2-acrylamido-2-methylpropanesulfonic acid (hereinafter referred to simply as AMPS monomer, a registered trademark of The Lubrizol Corporation). In this process, the starting material is crude AMPS monomer crystals which have been obtained by washing precipitates from the reaction mixture obtained by any of the conventional reaction methods. The crude crystals are dissolved in hydrous acetic acid containing 5 to 40% water. The quantity of the hydrous acetic acid required to completely dissolve the desired amount of AMPS monomer at 90° C. depends on the water content. When the hydrous acetic acid has a water content of 10%, it is used in an amount about 4 to 5 times the weight of crude crystals. The purified crystals are collected by filtration of this solution after the solution is cooled to about 10 to 20° C.

U.S. Pat. No. 4,701,283 (Itoh et al, Oct. 20, 1987) relates to a process for preparing amidoalkanesulfonic acids and derivatives, such as salts thereof, as well as copolymer-coated solid materials, copolymer emulsions and pigment dispersants in which the copolymer is obtained by copolymerizing such an amidoalkanesulfonic acid derivative with another monomer.

U.S. Pat. No. 4,650,614 (Jevne et al, Mar. 17, 1987) provides a method for purifying reaction grade 2-acrylamido-2-methylpropanesulfonic acid, as obtained commercially, by a short duration, mild heating of the acid in a slurry with a volatile liquid monohydric alcohol followed by acid recovery via decantation or other form of separation and subsequent drying of the wet solid acid.

SUMMARY OF THE INVENTION

The present invention is a process for the preparation of a purified monomer comprising the steps of reacting a substantially aqueous solution of an impure monomer (A)

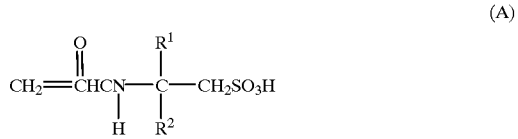

wherein $R^1$ and $R^2$ are independently hydrogen or alkyl groups containing from 1 to about 6 carbon atoms, with (B) a substantially aqueous solution of an oxide or hydroxide of the structure MO or MOH wherein M is a Group IA or Group IIA metal, or an amine of the structure $NR^3R^4R^5$ wherein $R^3$, $R^4$ and $R^5$ are independently hydrogen or alkyl, alkanol or alkoxy groups containing from 1 to about 12 carbon atoms, wherein the molar ratio of (A):(B) is from about 1:1–2 for Group IA metals, 2:1–2 for Group IIA metals or ratio of moles of (A) to nitrogens of (B) is from about 1:1–2 nitrogens to form a salt, and recovering a purified salt by crystallization by subjecting the aqueous solution to changes in temperature and/or pressure and/or concentration.

DETAILED DESCRIPTION OF THE INVENTION

Figure 1:
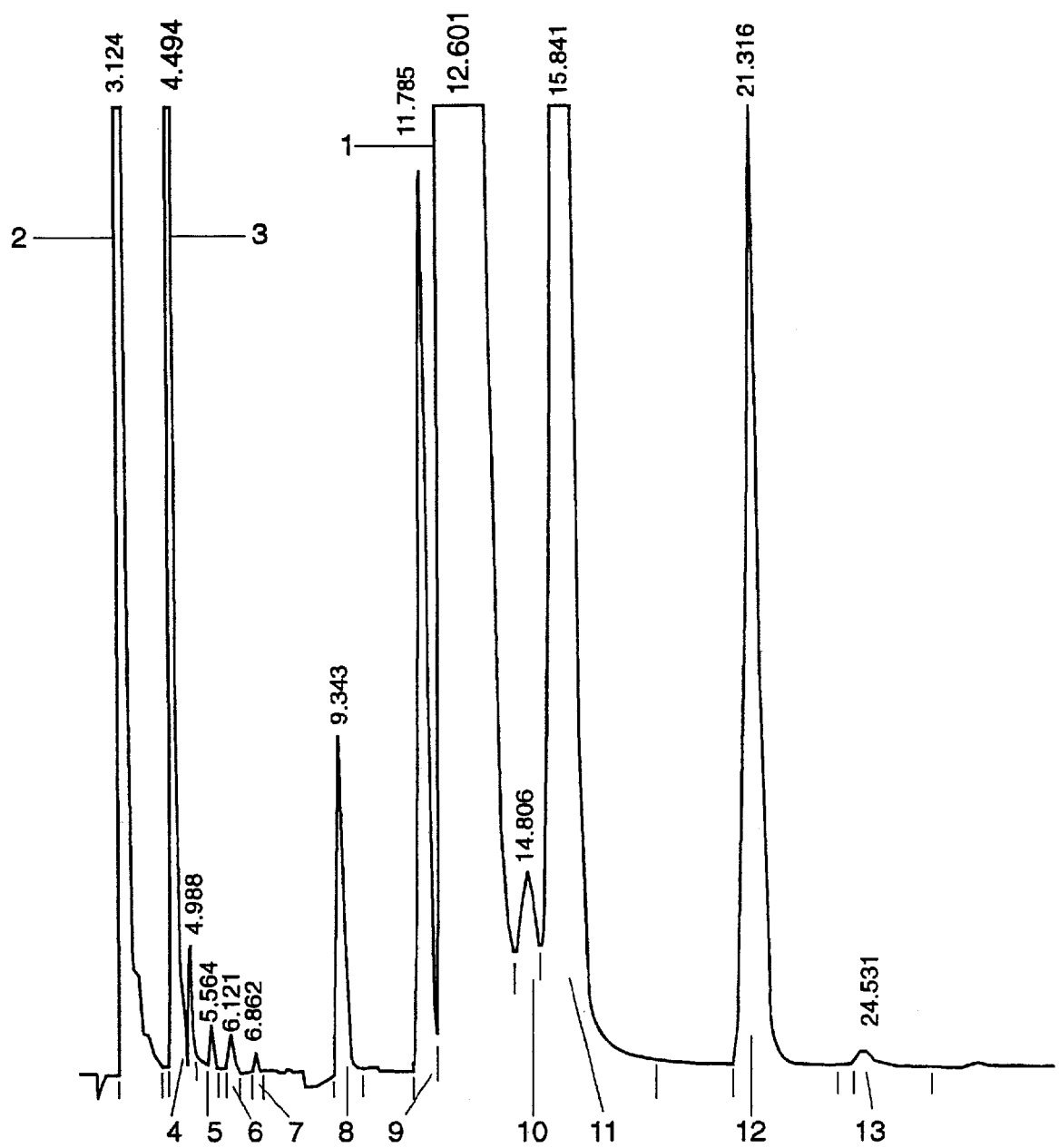
FIG. 1 is a chromatograph of impure AMPS monomer

Generally this invention provides a process for purifying a monomer of a sulfonic acid derivative. A substantially aqueous solution of a commercially obtained (A) monomer of a sulfonic acid is reacted with (B) a substantially aqueous solution of an oxide, hydroxide or an amine. The reaction of (A) and (B) forms a salt. The invention lies in being able to obtain a salt of high purity. This high purity salt has utility as a monomer to produce ultra high molecular weight copolymers or homopolymer of said monomer. The prepared polymers function as flocculants, fluid loss and cementing polymers.

(A) The Monomer of a Sulfonic Acid

The sulfonic acid

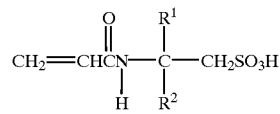

wherein $R^1$ and $R^2$ are as defined above can be prepared by several different schemes. One method involves reacting acrylonitrile with a B-hydroxyalkanesulfonic acid

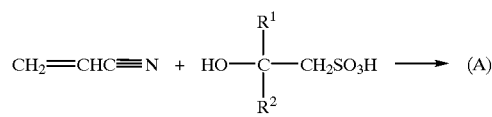

Another method involves reacting acrylonitrile with an olefin such as propylene or a butylene in the presence of fuming sulfuric acid.

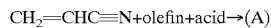

In any event, the (A) component is a starting material for this invention and as such is commercially readily available. The preferred (A) is one wherein $R^1$ and $R^2$ are both methyl groups to give 2-acrylamido-2-methyl-propanesulfonic acid.

(B) The Oxide, Hydroxide or Amine

Component (B) is a substantially aqueous solution of a metal oxide, MO; a metal hydroxide, MOH; or an amine. As a metal oxide or hydroxide, preferred are the Group IA and Group IIA metals as identified in the Periodic Table of the Elements published by Johnson Mattey, 1989. Specifically, these metals are lithium, sodium, potassium, magnesium and calcium. The most preferred Group IA metal is sodium and the most preferred Group IIA metal is magnesium. Of the metal oxide or hydroxide, it is preferred to employ a metal hydroxide, specifically sodium hydroxide.

Component (B) may also be a substantially aqueous solution of an amine $NR^3R^4R^5$ wherein $R^3$, $R^4$ and $R^5$ are independently hydrogen or alkyl, alkanol or alkoxy groups containing from 1 to about 12 carbon atoms, preferably from 1 to about 8 carbon atoms and most preferably from 1 to about 4 carbon atoms. It is most desirable to employ an aqueous solution of ammonia wherein $R^3=R^4=R^5=$hydrogen.

In an alternative embodiment, component (B) may be a substantially aqueous solution of an amine of the structure $R^3R^4NR^6NR^7$ wherein $R^3$ and $R^4$ are as defined above, $R^6$ is an alkylene group containing from 1 to about 6 carbon atoms and $R^7$ is $R^3R^4$ or $-CH_2CH_2XCH_2CH_2-$ wherein X is

or oxygen.

The term "substantially aqueous solution" means that water is the predominant solvent. Water comprises at least about 95%, and most preferably at least about 99% by weight of the solvent. Other solvents that may be present are alcohols, aldehydes, ketones, esters and ethers of 4 carbon atoms, or less, -amides such as dimethyl formamide or sulfoxides such as dimethyl sulfoxide.

When $R^3$, $R^4$ and $R^5$ are alkyl groups, an illustrative but non-exhaustive list is methyl, ethyl, n-propyl, isopropyl, n-butyl, 2-methylpropyl, n-pentyl, 2-methylbutyl, 3-methylbutyl, neopentyl, n-hexyl, 2-methylpentyl, 3-methylpentyl, 4-methylpentyl, 2-ethylbutyl, 3-ethylbutyl, 2,3-dimethylbutyl, 2,2-dimethylbutyl, 3,3-dimethylbutyl and the isomeric heptyls, octyls, nonyls, decyls, undecyls and dodecyls.

As alkanols, $R^3$, $R^4$ and $R^5$ are $-CH_2OH$, $-CH_2CH_2OH$,

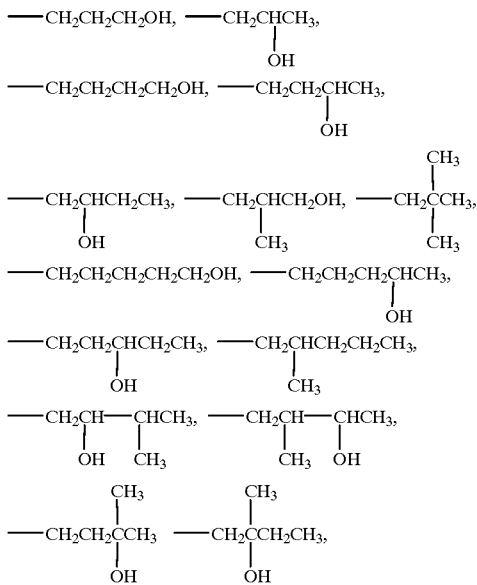

the isomeric hexanols, heptanols, octanols, nonanols, decanols, undecanols and dodecanols.

As alkoxy groups, $R^3$, $R^4$ and $R^5$ are $-OCH_3$, $-OCH_2CH_3$,

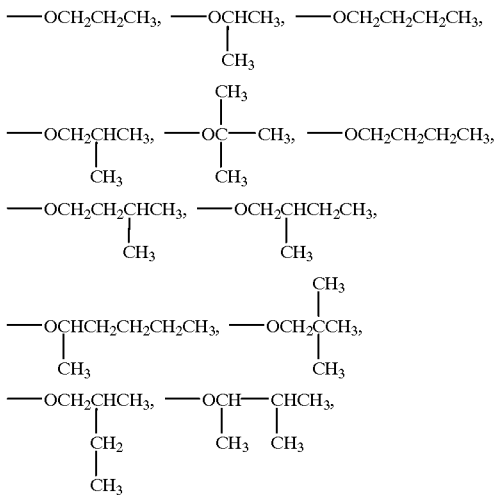

the isomeric hexoxys, heptoxys, octoxys, nonoxys, decoxys, undecoxys and dodecoxys.

When the amine is $R^3R^4NR^6NR^7$, $R^3$ and $R^4$ are as earlier defined and $R^6$ is an alkylene group containing from 1 to about 6 carbon atoms, preferably from 1 to about 3 carbon atoms. $R^6$ may be methylene, ethylene, or isomers of propylene, butylene, pentylene or hexylene, Most preferably, $R^6$ is ethylene. $R^7$ is $R^3R^4$ or $-CH_2CH_2XCH_2CH_2-$ wherein X is

or oxygen.

Some of the preferred amines of the formula $R^3R^4NR^6NR^7$ are $H_2NCH_2CH_2NH_2$, $H_2NCH_2CH_2CH_2NH_2$, $CH_3NHCH_2CH_2NH_2$,

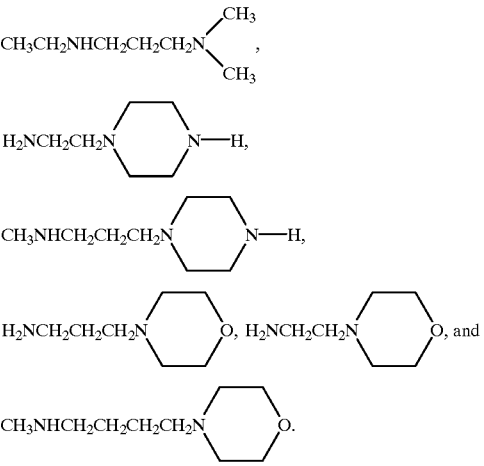

No attempt is made to purify component (A) prior to salt formation. Component (B) is typically prepared in an aqueous solution. Component (A) may be in aqueous solution or substantially aqueous free. By substantially aqueous free it is meant that free water is present at no more than about 2%, d preferably, no more than about 1% on a weight basis.

The reaction of component (A) with component (B) produces a salt. There is no criticality in employing an extremely large excess of (B). From as little as 1 mole percent excess up to about 20 mole percent excess is envisaged.

Component (B3) is an aqueous solutions having a percent weight of water of from about 15 to about 95, preferably from about 25 to about 95 and most preferably from about 50 to about 90.

To effect salt formation, component (A) may be added to component (B) or vice-versa. In practice, component (A) is usually added to component (B). Salt formation is exothermic and the exotherm is utilized to solubilize the maximum amount of salt in water. After the salt is formed in an aqueous medium, it is filtered to remove any solid impurities. The aqueous salt is then cooled and the solid salt is obtained as a purified product by crystallization.

The reaction of (A) and (B) to form a salt occurs at a temperature of from about −20° C. up to about the decomposition of any reactant or product. Preferably, the salt formation is conducted at a temperature of from about 20° C. up to about 75° C. and most preferably from about 30° C. up to about 75° C.

The molar ratio of (A):(B) to effect salt formation is dependent on the nature of (B). When (B) is a Group IA metal, the molar ratio of (A):(B) is from about 1:1–2, preferably 1:1–1.10 and most preferably from about 1:1–1.05. When (B) is a Group IIA metal, the molar ratio of (A):(B) is from about 2:1–2, preferably 2:1–1.10 and most preferably from about 2:1–1.05. When B is an amine of the formula $NR^3R^4R^5$, the ratio of moles of (A) to nitrogens of (B) is from about 1:1–2, preferably 1:1–1.10 and most preferably from about 1:1–1.05. When B is an amine of the formula $R^3R^4 NR^6NR^7$ the ratio of moles of (A) to nitrogens of (B) is from about 2:2–3, preferably 2:2–2.1 and most preferably from about 2:2–2.05. However, when

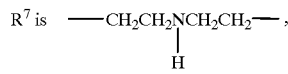

then the ratio of moles of (A) to nitrogens of (B) is from about 3:3–4, preferably 3:3–3.1 and most preferably from about 3:3–3.05.

The salt so formed is in aqueous solution. The aqueous solution is filtered to remove solid impurities, and the salt is recovered by subjecting the aqueous solution to changes in temperature and/or pressure and/or concentration. By increasing the temperature, water is removed which increases the amount of salt present relative to the remaining water. Removal of water at an increased temperature may be facilitated by decreasing the pressure. However, water may also be removed by decreasing the pressure even at ambient temperature. By decreasing the temperature, the salt is removed due to a shift in the solubility of salt relative to temperature.

At any rate, the salt is recovered by effecting supersaturation. The two methods for providing supersaturation are the thermal swing and evaporative crystallization. In the thermal swing, a saturated solution is cooled to reduce the solubility of the desired salt. As the solubility is decreased, the salt is crystallized out of solution. In the evaporative crystallization, water is removed from the aqueous solution either through heating or reduced pressure or a combination of heating and reduced pressure. Less water present to effect solution causes the desired salt to crystallize. The thermal swing and evaporative crystallization may be carried out batchwise or continuously.

Component (A) is a known monomer in the polymer field. The salt of (A) and (B) also has utility as a monomer. As such, it becomes necessary to ensure that neither (A) nor the salt do not undergo polymerization or any other undesired reaction. Care must be taken in recovering the monomeric salt of (A) and (B). Unlike the recovery of a non-monomeric material, certain conditions of temperature, pH and the presence of an oxygen bearing gas are necessary. These conditions are necessary in order to prevent polymerization of (A) and/or the monomeric salt.

It is necessary that the aqueous solution be maintained at a temperature of between about −20° C. to about 75° C. Temperatures above about 77° C. lead to rapid formation of by-products by the addition of water across the double bond in component (A) which is an undersired reaction. Temperatures above about 77° C. also leads to some salt polymer formation. Temperatures below about −20° C. cause the formation of ice crystals which cause problems during separation of the salt from the aqueous solution.

The pH of the aqueous salt solution is to be maintained at between about 7 to about 12.5 A pH of less than 7 causes rapid polymerization of either (A) or the salt or both and a pH of greater than 12.5 causes rapid by-product formation at temperatures above 75° C. A pH of less than 7 is caused by an excessive amount of unreacted AMPS monomer. This is corrected by the addition of component (B). A pH of greater than 12.5 is caused by an excessive amount of component (B). This condition is corrected by the addition of more AMPS monomer.

In order to prevent polymerization of (A), the salt or both or to prevent undesired side reactions, it is necessary to maintain both temperature and pH, as discussed above. It is also helpful to utilize a polymerization inhibitor. Many polymerization inhibitors are available. An especially preferred polymerization inhibitor is hydroquinone monomethyl ether. This inhibitor requires the presence of dissolved oxygen in the aqueous solution in order to be effective. During the evaporative crystallization water is distilled away under reduced pressure in order to lower the distillation temperature and minimize by-product formation. A constant purge of air or any other oxygen bearing gas stream to the distillation vessel must be maintained or polymerization will occur. Polymerization will also occur if water is evaporated to dryness.

The following examples illustrate preparation of the salt.

EXAMPLE 1

In a 2-liter flask is prepared a solution of 87.2 parts (2.18 moles) sodium hydroxide in 461 parts water and purged with compressed air at 0.5 cubic feet per hour. To this solution is slowly added 452 parts (2.18 moles) AMPS monomer and 0.07 part hydroquinone monomethyl ether in 400 parts water while stirring and maintaining the air purge. The temperature is maintained at between about 24–40° C. The contents are then filtered to remove insolubles prior to crystallization.

EXAMPLE 2

Charged to a 5-liter flask is a solution of 124 parts (3.1 moles) sodium hydroxide and 0.13 parts hydroquinone monomethyl ether in 400 parts water. This is followed by the addition of 100 parts of an aqueous solution of impure AMPS monomer prepared by reacting isobutylene and acrylonitrile in the presence of fuming sulfuric acid. This solution contains 3.05 moles AMPS monomer based on a neutralization number to phenolphthalein of 275. In the chromatograph of FIG. 1, AMPS monomer is identified at 1.

The impurities of this AMPS monomer are identified at 2–13. The amount of impurity is a function of the area under 2–13 relative to the area under 1. Air is bubbled below the surface at 0.5 cubic feet per hour while maintaining the temperature at between 30–50° C. The contents are filtered to remove insolubles prior to crystallization.

Table I outlines Examples 3–8 wherein 1000 parts of an impure aqueous solution of AMPS monomer as defined in Example 2 is reacted with various metal oxides or metal hydroxides as component (B) to form the salt. These procedures are according to Example 2.

TABLE I

| Example | Moles AMPS Monomer | Moles-Component (B) in 400 Parts water | Temperature Range ° C. |
|---|---|---|---|
| 3 | 3.05 | 3.15 - KOH | 40–60 |
| 4 | 3.05 | 1.6 - Ca(OH)$_2$ | 35–60 |
| 5 | 3.05 | 1.55 - MgO | 30–60 |
| 6 | 3.05 | 3.1 - LiOH | 40–65 |
| 7 | 3.05 | 1.6 - CaO | 40–65 |
| 8 | 3.05 | 1.55 - Li$_2$O | 35–55 |

Table II outlines Examples 9–17 wherein 1000 parts of an impure aqueous solution of AMPS monomer as defined in Example 2 is reacted with various amines of the structure $NR^3R^4R^5$ to form the salt. These procedures are according to Example 2.

The following examples illustrate purification of the salt by crystallization by both the thermal swing and evaporation crystallization methods.

EXAMPLE 26

Thermal Swing

Figure 2:
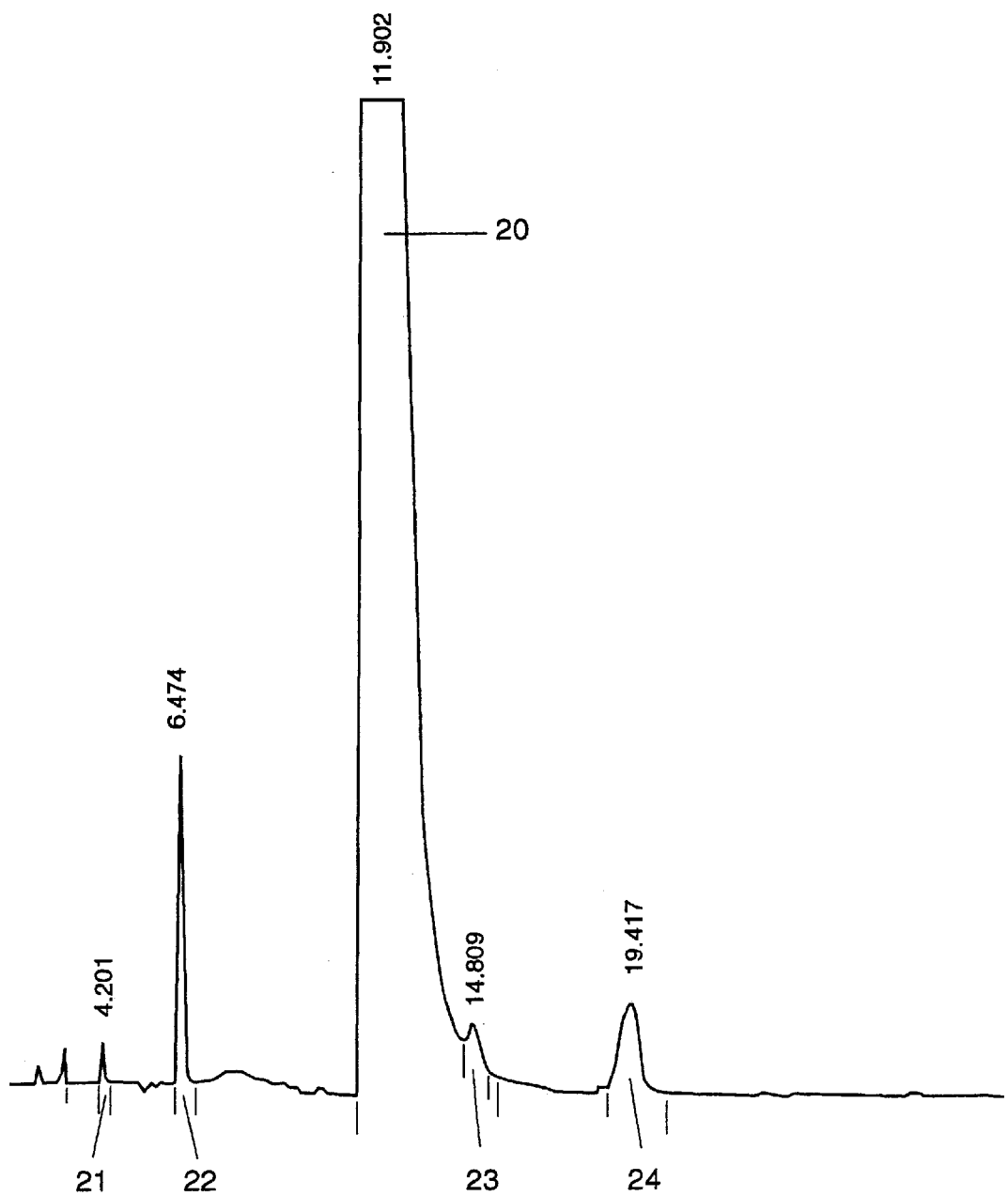
FIG. 2 is a chromatograph of a purified sodium salt of AMPS monomer.

The filtered contents of Example 2 are added to a 5-liter flask immersed in a bath set up with coils for cooling. Air is blown below the surface at 0.25 cubic feet per hour and stirring is begun. The contents of the flask are cooled to −10° C. by pumping brine through the cooling coils. The temperature is maintained at −10° C. for 8 hours. The contents are filtered through paper and the product is obtained as a solid having the following analyses: % sodium 9.91, % sulfur 13.92, % nitrogen 6.05. In the chromatograph of FIG. 2, the sodium salt of AMPS monomer is identified at 20. The impurities are identified at 21–24. In comparing FIG. 2, the purified salt of Example 26, with FIG. 1, the impure starting material, it is readily apparent that the impurities 21–24 residing with the purified salt are both less in number and in relative concentration to the starting material impurities 2–13.

EXAMPLE 27

Evaporative Crystallization

The filtered contents of Example 2 are added to a 3-liter flask equipped for distillation and containing an air purge

TABLE II

| Example | Moles AMPS Monomer | Moles $NR^3R^4R^5$ in 400 parts water | $R^3$ | $R^4$ | $R^5$ | Temperature Range ° C. |
|---|---|---|---|---|---|---|
| 9 | 4.0 | 4.1 | H | H | H | 40–65 |
| 10 | 4.0 | 4.1 | H | H | —CH$_3$ | 40–65 |
| 11 | 4.0 | 4.2 | H | H | —CH$_2$CH$_3$ | 40–65 |
| 12 | 4.0 | 4.1 | H | —CH$_3$ | —CH$_3$ | 40–65 |
| 13 | 4.0 | 4.05 | —CH$_3$ | —CH$_3$ | —CH$_3$ | 40–65 |
| 14 | 4.0 | 4.1 | H | H | —CH$_2$OH | 40–65 |
| 15 | 4.0 | 4.1 | H | H | —OCH$_3$ | 40–65 |
| 16 | 4.0 | 4.1 | H | H | —CH$_2$CH$_2$OH | 40–65 |
| 17 | 4.0 | 4.1 | H | H | —OCH$_2$CH$_3$ | 40–65 |

Table III outlines Examples 18–25 wherein 1000 parts of an impure aqueous solution of AMPS monomer as defined in Example 2 is reacted with various amines of the structure $R^3R^4NR^6NR^7$ to form the salt. These procedures according to Example 2. The temperature range is from about 40–65° C.

tube. The contents are heated and stirred while air is blown below the surface at 0.5 cubic feet per hour. The contents are heated to 50° C. while under a vacuum of 700 millimeters of mercury. As water is removed, more and more solids appear in the flask. Water is removed until that point where stirring becomes difficult. The contents are then transferred

TABLE III

| Example | Moles AMPS Monomer | Moles $R^3R^4NR^6NR^7$ in 400 parts water | $R^3$ | $R^4$ | $R^6$ | $R^7$ |
|---|---|---|---|---|---|---|
| 19 | 4.0 | 2.05 | H | H | —CH$_2$CH$_2$— | H, H |
| 20 | 4.0 | 2.05 | H | H | —CH$_2$CH$_2$— | H, —CH$_3$ |
| 21 | 4.0 | 2.05 | H | H | —CH$_2$CH$_2$CH$_2$— | H, H |
| 22 | 4.0 | 2.05 | H | H | —CH$_2$CH$_2$— | H, —CH$_2$CH$_2$OH |
| 23 | 4.0 | 2.05 | H | H | —CH$_2$CH$_2$CH$_2$— | H, —OCH$_2$CH$_3$ |
| 24 | 4.0 | 2.05 | H | H | —CH$_2$CH$_2$CH$_2$— | —CH$_2$CH$_2$OCH$_2$CH$_2$— |
| 25 | 4.0 | 1.37 | H | H | —CH$_2$CH$_2$CH$_2$— | —CH$_2$CH$_2$NCH$_2$CH$_2$—<br>\|<br>H | to a centrifuge where the solid product is obtained having the following analyses: % sodium 9.94, % sulfur 13.89, % nitrogen 6.03.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A process for the preparation of a purified monomer comprising the steps of reacting a substantially aqueous solution of an impure monomer

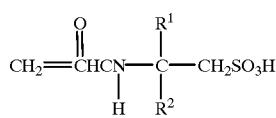

(A)

wherein $R^1$ and $R^2$ are independently hydrogen or alkyl groups containing from 1 to about 6 carbon atoms, with (B) a substantially aqueous solution of an oxide or hydroxide of the structure MO or MOH wherein M is a Group IA or Group IIA metal, or an amine of the structure $NR^3R^4R^5$ wherein $R^3$, $R^4$ and $R^5$ are independently hydrogen or alkyl, alkanol or alkoxy groups containing from 1 to about 12 carbon atoms, wherein the molar ratio of (A):(B) is from about 1:1–2 for Group IA metals, 2:1–2 for Group IIA metals or ratio of moles of (A) to nitrogens of (B) is from about 1:1–2 nitrogens to form a salt, wherein in order to prevent polymerization of (A), the purified monomer or both or to prevent undesired side reactions, the reaction of (A) and (B) occurs at a temperature of between about −20 to 75° C. and at a pH between 7 to 12.5, and recovering a purified salt by crystallization in the presence of an oxygen bearing gas stream either by removing water from the aqueous solution by subjecting the aqueous solution to an increase in temperature and/or a decrease in pressure or by decreasing the solubility of the salt in the aqueous solution by subjecting the aqueous solution to a decrease in temperature.

2. A process according to claim 1 wherein the Group I metals are lithium, sodium or potassium.

3. The process according to claim 1 wherein the Group II metals are magnesium or calcium.

4. The process according to claim 1 wherein the molar ratio of (A):(B) is from about 1:1–1.05 for Group IA metals to form a salt.

5. The process according to claim 1 wherein $R^1$ and $R^2$ are independently methyl, ethyl or propyl.

6. The process according to claim 1 wherein $R^3$, $R^4$ and $R^5$ are independently hydrogen or alyl, alkanol or alkoxy groups containing from 1 to about 12 carbon atoms.

7. The process according to claim 1 wherein the purified salt is recovered by removing water from the aqueous solution by subjecting the aqueous solution to an increase in temperature.

8. The process according to claim 1 wherein the Group IA metal is sodium.

9. The process according to claim 1 wherein the Group IIA metal is magnesium.

10. The process according to claim 1 wherein the purified salt is recovered by removing water from the aqueous solution by subjecting the aqueous solution to a decrease in pressure.

11. The process according to claim 6 wherein $R^3$, $R^4$ and $R^5$ are independently hydrogen or alkyl, alkanol or alkoxy groups containing from 1 to about 8 carbon atoms.

12. The process according to claim 4 wherein $R^1$ and $R^2$ are methyl.

13. The process according to claim 1 wherein the molar ratio of (A):(B) is from about 2:1–1.05 for Group II metals to form a salt.

14. The process according to claim 11 wherein $R^3$, $R^4$ and $R^5$ are independently hydrogen or alkyl, alkanol or alkoxy groups containing from 1 to about 4 carbon atoms.

15. The process according to claim 1 wherein the ratio of moles of (A) to nitrogens of (B) is from about 1:1–1.05 to form a salt.

16. The process according to claim 1 wherein the purified salt is recovered by removing water from the aqueous solution by decreasing the solubility of the salt in the aqueous solution by subjecting the aqueous solution to a decrease in temperature.

17. The process according to claim 14 wherein $R^3$, $R^4$ and $R^5$ are hydrogen.

18. The process according to claim 1 wherein $R^1$ and $R^2$ are methyl, (B) is NaOH and the molar ratio of (A):(B) is from about 1:1–1.05.

* * * * *